US008465487B2

(12) United States Patent
Suslov

(10) Patent No.: US 8,465,487 B2
(45) Date of Patent: Jun. 18, 2013

(54) PLASMA-GENERATING DEVICE HAVING A THROTTLING PORTION

(75) Inventor: Nikolay Suslov, Atlanta, GA (US)

(73) Assignee: Plasma Surgical Investments Limited, Tortola (VG)

( * ) Notice: Subject to any disclaimer, the term of this patent is extended or adjusted under 35 U.S.C. 154(b) by 0 days.

(21) Appl. No.: 13/357,895

(22) Filed: Jan. 25, 2012

(65) Prior Publication Data

US 2012/0143183 A1 Jun. 7, 2012

Related U.S. Application Data

(63) Continuation of application No. 11/482,582, filed on Jul. 7, 2006, now Pat. No. 8,105,325.

(30) Foreign Application Priority Data

Jul. 8, 2005 (SE) ...................................... 0501602

(51) Int. Cl.
*A61B 18/14* (2006.01)

(52) U.S. Cl.
USPC .............................................. 606/45; 606/39

(58) Field of Classification Search
USPC ............................................... 606/40, 45, 49
See application file for complete search history.

(56) References Cited

U.S. PATENT DOCUMENTS

| | | | |
|---|---|---|---|
| 3,077,108 | A | 2/1963 | Gage et al. |
| 3,082,314 | A | 3/1963 | Arata et al. |
| 3,100,489 | A | 8/1963 | Bagley |
| 3,145,287 | A | 8/1964 | Seibein et al. |
| 3,153,133 | A | 10/1964 | Ducati |
| 3,270,745 | A | 9/1966 | Wood |
| 3,360,988 | A | 1/1968 | Stein et al. |
| 3,413,509 | A | 11/1968 | Cann et al. |
| 3,433,991 | A | 3/1969 | Whyman |
| 3,434,476 | A | 3/1969 | Shaw et al. |
| 3,534,388 | A | 10/1970 | Akiyama et al. |
| 3,628,079 | A | 12/1971 | Dobbs et al. |
| 3,676,638 | A | 7/1972 | Stand |

(Continued)

FOREIGN PATENT DOCUMENTS

| | | |
|---|---|---|
| AU | 2000250426 | 6/2005 |
| AU | 2006252145 | 1/2007 |

(Continued)

OTHER PUBLICATIONS

U.S. Appl. No. 13/358,934, filed Jan. 26, 2012, Suslov.

(Continued)

*Primary Examiner* — Linda Dvorak
*Assistant Examiner* — Jaymi Della
(74) *Attorney, Agent, or Firm* — Jones Day

(57) ABSTRACT

The present invention relates to a plasma-generating device comprising an anode, a cathode, and intermediate electrodes. The intermediate electrodes and the anode form an elongate plasma channel that extends from a point between the cathode and the anode and through the anode. The plasma channel has a throttling portion with a throat having the smallest cross-sectional area of the entire plasma channel. As a plasma flow passes through the throttling portion, the plasma flow's speed is increased while its pressure is decreased. By varying the position of the throttling portion in the plasma channel properties of the discharged plasma can be changed. Plasma flows with different properties can be used for various applications, especially, medical procedures.

22 Claims, 4 Drawing Sheets

U.S. PATENT DOCUMENTS

| | | | |
|---|---|---|---|
| 3,775,825 A | 12/1973 | Wood et al. | |
| 3,803,380 A | 4/1974 | Ragaller | |
| 3,838,242 A | 9/1974 | Goucher | |
| 3,851,140 A | 11/1974 | Coucher | |
| 3,866,089 A * | 2/1975 | Hengartner | 315/111.21 |
| 3,903,891 A | 9/1975 | Brayshaw | |
| 3,914,573 A | 10/1975 | Muehlberger | |
| 3,938,525 A | 2/1976 | Coucher | |
| 3,991,764 A | 11/1976 | Incropera et al. | |
| 3,995,138 A | 11/1976 | Kalev et al. | |
| 4,029,930 A | 6/1977 | Sagara et al. | |
| 4,035,684 A | 7/1977 | Svoboda et al. | |
| 4,041,952 A | 8/1977 | Morrison, Jr. et al. | |
| 4,201,314 A | 5/1980 | Samuels et al. | |
| 4,256,779 A | 3/1981 | Sokol et al. | |
| 4,317,984 A | 3/1982 | Fridlyand | |
| 4,397,312 A | 8/1983 | Molko | |
| 4,445,021 A | 4/1984 | Irons et al. | |
| 4,620,080 A | 10/1986 | Arata et al. | |
| 4,661,682 A | 4/1987 | Gruner et al. | |
| 4,672,163 A | 6/1987 | Matsui et al. | |
| 4,674,683 A | 6/1987 | Fabel | |
| 4,682,598 A | 7/1987 | Beraha | |
| 4,696,855 A | 9/1987 | Pettit, Jr. et al. | |
| 4,711,627 A | 12/1987 | Oeschsle et al. | |
| 4,713,170 A | 12/1987 | Saibic | |
| 4,743,734 A | 5/1988 | Garlanov et al. | |
| 4,764,656 A | 8/1988 | Browning | |
| 4,777,949 A | 10/1988 | Perlin | |
| 4,780,591 A | 10/1988 | Bernecki et al. | |
| 4,781,175 A | 11/1988 | Mcgreevy et al. | |
| 4,784,321 A | 11/1988 | Delaplace | |
| 4,785,220 A | 11/1988 | Brown et al. | |
| 4,839,492 A | 6/1989 | Bouchier et al. | |
| 4,841,114 A | 6/1989 | Browning | |
| 4,853,515 A | 8/1989 | Willen et al. | |
| 4,855,563 A | 8/1989 | Beresnev et al. | |
| 4,866,240 A | 9/1989 | Webber | |
| 4,869,936 A | 9/1989 | Moskowitz et al. | |
| 4,874,988 A | 10/1989 | English | |
| 4,877,937 A | 10/1989 | Muller | |
| 4,916,273 A | 4/1990 | Browning | |
| 4,924,059 A | 5/1990 | Rotolico et al. | |
| 5,008,511 A | 4/1991 | Ross | |
| 5,013,883 A | 5/1991 | Fuimefreddo et al. | |
| 5,100,402 A | 3/1992 | Fan | |
| 5,144,110 A | 9/1992 | Marantz et al. | |
| 5,151,102 A | 9/1992 | Kamiyama et al. | |
| 5,201,900 A | 4/1993 | Nardella | |
| 5,207,691 A | 5/1993 | Nardella | |
| 5,211,646 A | 5/1993 | Alperovich et al. | |
| 5,217,460 A | 6/1993 | Knoepfler | |
| 5,225,652 A | 7/1993 | Landes | |
| 5,227,603 A | 7/1993 | Doolette et al. | |
| 5,261,905 A | 11/1993 | Doresey | |
| 5,285,967 A | 2/1994 | Weidman | |
| 5,332,885 A | 7/1994 | Landes | |
| 5,352,219 A | 10/1994 | Reddy | |
| 5,396,882 A | 3/1995 | Zapol | |
| 5,403,312 A | 4/1995 | Yates et al. | |
| 5,406,046 A | 4/1995 | Landes | |
| 5,408,066 A | 4/1995 | Trapani et al. | |
| 5,412,173 A | 5/1995 | Muehlberger | |
| 5,445,638 A | 8/1995 | Rydell et al. | |
| 5,452,854 A | 9/1995 | Keller | |
| 5,460,629 A | 10/1995 | Shlain et al. | |
| 5,485,721 A | 1/1996 | Steenborg | |
| 5,514,848 A | 5/1996 | Ross et al. | |
| 5,519,183 A | 5/1996 | Mueller | |
| 5,527,313 A | 6/1996 | Scott et al. | |
| 5,573,682 A | 11/1996 | Beason, Jr. | |
| 5,582,611 A | 12/1996 | Tsuruta et al. | |
| 5,620,616 A | 4/1997 | Anderson et al. | |
| 5,629,585 A | 5/1997 | Altmann | |
| 5,637,242 A | 6/1997 | Muehlberger | |
| 5,640,843 A | 6/1997 | Aston | |
| 5,662,680 A | 9/1997 | Desai | |
| 5,665,085 A | 9/1997 | Nardella | |
| 5,679,167 A | 10/1997 | Muehlberger | |
| 5,680,014 A | 10/1997 | Miyamoto et al. | |
| 5,688,270 A | 11/1997 | Yates et al. | |
| 5,697,281 A | 12/1997 | Eggers et al. | |
| 5,697,882 A | 12/1997 | Eggers et al. | |
| 5,702,390 A | 12/1997 | Austin et al. | |
| 5,720,745 A | 2/1998 | Farin et al. | |
| 5,733,662 A | 3/1998 | Bogachek | |
| 5,797,941 A | 8/1998 | Schulze et al. | |
| 5,827,271 A | 10/1998 | Buysse et al. | |
| 5,833,690 A | 11/1998 | Yates et al. | |
| 5,837,959 A | 11/1998 | Muehlberger et al. | |
| 5,843,079 A | 12/1998 | Suslov | |
| 5,858,469 A | 1/1999 | Sahoo et al. | |
| 5,858,470 A | 1/1999 | Bernecki et al. | |
| 5,897,059 A | 4/1999 | Muller | |
| 5,906,757 A * | 5/1999 | Kong et al. | 219/121.47 |
| 5,932,293 A | 8/1999 | Belashchenko et al. | |
| 6,003,788 A | 12/1999 | Sedov | |
| 6,042,019 A | 3/2000 | Rusch | |
| 6,099,523 A | 8/2000 | Kim et al. | |
| 6,114,649 A | 9/2000 | Delcea | |
| 6,135,998 A | 10/2000 | Palanker | |
| 6,137,078 A | 10/2000 | Keller | |
| 6,137,231 A | 10/2000 | Anders | |
| 6,162,220 A | 12/2000 | Nezhat | |
| 6,169,370 B1 * | 1/2001 | Platzer | 315/111.21 |
| 6,181,053 B1 | 1/2001 | Roberts | |
| 6,202,939 B1 | 3/2001 | Delcea | |
| 6,273,789 B1 | 8/2001 | Lasalle et al. | |
| 6,283,386 B1 | 9/2001 | Van steenkiste et al. | |
| 6,322,856 B1 | 11/2001 | Hislop | |
| 6,352,533 B1 | 3/2002 | Ellman et al. | |
| 6,386,140 B1 | 5/2002 | Muller et al. | |
| 6,392,189 B1 | 5/2002 | Delcea | |
| 6,443,948 B1 | 9/2002 | Suslov et al. | |
| 6,475,212 B2 | 11/2002 | Dobak | |
| 6,475,215 B1 | 11/2002 | Tanrisever | |
| 6,514,252 B2 | 2/2003 | Nezhat et al. | |
| 6,528,947 B1 | 3/2003 | Chen et al. | |
| 6,548,817 B1 | 4/2003 | Anders | |
| 6,562,037 B2 | 5/2003 | Paton et al. | |
| 6,629,974 B2 | 10/2003 | Penny et al. | |
| 6,634,571 B2 | 10/2003 | Shimazu | |
| 6,636,545 B2 | 10/2003 | Krasnov | |
| 6,657,152 B2 | 12/2003 | Shimazu | |
| 6,669,106 B2 | 12/2003 | Delcea | |
| 6,676,655 B2 | 1/2004 | Mcdaniel et al. | |
| 6,780,184 B2 | 8/2004 | Tanrisever | |
| 6,808,525 B2 | 10/2004 | Latterell et al. | |
| 6,811,812 B2 | 11/2004 | Van Steenkiste | |
| 6,844,560 B2 | 1/2005 | Wieland et al. | |
| 6,845,929 B2 | 1/2005 | Dolatabadi et al. | |
| 6,886,757 B2 | 5/2005 | Byrnes et al. | |
| 6,958,063 B1 | 10/2005 | Soll et al. | |
| 6,971,989 B2 | 12/2005 | Yossepowitch | |
| 6,972,138 B2 | 12/2005 | Heinrich et al. | |
| 6,986,471 B1 | 1/2006 | Kowalsky et al. | |
| 7,025,764 B2 | 4/2006 | Paton et al. | |
| 7,030,336 B1 | 4/2006 | Hawley | |
| 7,118,570 B2 | 10/2006 | Tetzlaff et al. | |
| 7,132,619 B2 | 11/2006 | Conway | |
| 7,216,814 B2 | 5/2007 | Gardega | |
| 7,261,556 B2 | 8/2007 | Belashchenko et al. | |
| 7,276,065 B2 | 10/2007 | Morley et al. | |
| 7,291,804 B2 | 11/2007 | Suslov | |
| 7,316,682 B2 | 1/2008 | Konesky | |
| 7,361,175 B2 | 4/2008 | Suslov | |
| 7,431,721 B2 | 10/2008 | Paton et al. | |
| 7,491,907 B2 | 2/2009 | Kowalsky et al. | |
| 7,540,873 B2 | 6/2009 | Bayat | |
| 7,557,324 B2 | 7/2009 | Nylen et al. | |
| 7,582,846 B2 | 9/2009 | Molz et al. | |
| 7,589,473 B2 | 9/2009 | Suslov | |
| 7,608,797 B2 | 10/2009 | Belashchenko et al. | |
| 7,621,930 B2 | 11/2009 | Houser et al. | |
| 7,854,735 B2 | 12/2010 | Houser et al. | |
| 7,892,609 B2 | 2/2011 | Muller | |
| 7,928,338 B2 | 4/2011 | Suslov | |

| | | | | |
|---|---|---|---|---|
| 7,955,328 | B2 | 6/2011 | Long et al. | |
| 8,030,849 | B2 | 10/2011 | Suslov | |
| 8,105,325 | B2 | 1/2012 | Suslov | |
| 8,109,928 | B2 | 2/2012 | Suslov | |
| 2002/0071906 | A1 | 6/2002 | Rusch | |
| 2003/0125728 | A1 | 7/2003 | Nezhat et al. | |
| 2004/0068304 | A1 | 4/2004 | Paton et al. | |
| 2004/0124256 | A1 | 7/2004 | Itsukaichi et al. | |
| 2005/0192610 | A1 | 9/2005 | Houser et al. | |
| 2005/0192611 | A1 | 9/2005 | Houser | |
| 2005/0192612 | A1 | 9/2005 | Houser et al. | |
| 2006/0049149 | A1 | 3/2006 | Shimazu | |
| 2006/0091117 | A1 | 5/2006 | Blankenship et al. | |
| 2006/0091119 | A1 | 5/2006 | Zajchowski et al. | |
| 2006/0108332 | A1 | 5/2006 | Belashchenko | |
| 2006/0189976 | A1* | 8/2006 | Karni et al. | 606/41 |
| 2006/0217706 | A1 | 9/2006 | Lau et al. | |
| 2007/0029292 | A1 | 2/2007 | Suslov | |
| 2007/0173872 | A1 | 7/2007 | Neuenfeldt | |
| 2008/0015566 | A1 | 1/2008 | Livneh | |
| 2008/0071206 | A1 | 3/2008 | Peters | |
| 2008/0246385 | A1 | 10/2008 | Schamiloglu et al. | |
| 2009/0039789 | A1 | 2/2009 | Nikolay | |
| 2011/0190752 | A1 | 8/2011 | Suslov | |
| 2012/0022522 | A1 | 1/2012 | Suslov | |

FOREIGN PATENT DOCUMENTS

| | | | |
|---|---|---|---|
| CA | 983586 | | 2/1979 |
| CA | 1144104 | | 4/1983 |
| CA | 1308722 | | 10/1992 |
| CA | 2594515 | | 7/2006 |
| CN | 85107499 | B | 4/1987 |
| CN | 1331836 | | 1/2002 |
| CN | 1557731 | | 12/2004 |
| CN | 1682578 | A | 10/2005 |
| DE | 2033072 | | 2/1971 |
| DE | 10127261 | | 9/1993 |
| DE | 4209005 | | 12/2002 |
| EP | 0411170 | | 2/1991 |
| EP | 0748149 | | 12/1996 |
| EP | 0851040 | | 7/1998 |
| EP | 1293169 | | 3/2003 |
| EP | 1570798 | | 9/2005 |
| ES | 2026344 | | 4/1992 |
| FR | 2193299 | | 2/1974 |
| FR | 2567747 | | 1/1986 |
| GB | 751735 | | 7/1956 |
| GB | 921016 | | 3/1963 |
| GB | 1125806 | | 9/1968 |
| GB | 1176333 | | 1/1970 |
| GB | 1268843 | | 3/1972 |
| GB | 2407050 | | 4/2005 |
| JP | 47009252 | | 3/1972 |
| JP | 52-117255 | A | 10/1977 |
| JP | 54120545 | | 2/1979 |
| JP | 57001580 | | 1/1982 |
| JP | 57068269 | | 4/1982 |
| JP | 61013600 | | 1/1986 |
| JP | A-S61-193783 | | 8/1986 |
| JP | A-S61-286075 | | 12/1986 |
| JP | 62123004 | | 6/1987 |
| JP | 1198539 | | 8/1989 |
| JP | 1-319297 | A | 12/1989 |
| JP | 1319297 | | 12/1989 |
| JP | 3043678 | | 2/1991 |
| JP | 06262367 | | 9/1994 |
| JP | 9299380 | | 11/1997 |
| JP | 10024050 | | 1/1998 |
| JP | 10234744 | | 9/1998 |
| JP | 2002541902 | | 12/2002 |
| JP | 2005539143 | | 12/2005 |
| JP | 2008036001 | | 2/2008 |
| JP | 2008-284580 | A | 11/2008 |
| MX | PA04010281 | | 6/2005 |
| RU | 2178684 | | 1/2002 |
| RU | 2183480 | | 6/2002 |
| RU | 2183946 | | 6/2002 |
| WO | WO 92/19166 | | 11/1992 |
| WO | WO 96/06572 | | 3/1996 |
| WO | WO 97/11647 | | 4/1997 |
| WO | WO 01/62169 | | 8/2001 |
| WO | WO 02/30308 | | 4/2002 |
| WO | WO 03/028805 | | 4/2003 |
| WO | WO 2004/028221 | | 4/2004 |
| WO | WO 2004/030551 | | 4/2004 |
| WO | WO 2004/105450 | | 12/2004 |
| WO | WO 2005/099595 | | 10/2005 |
| WO | WO 2006/012165 | | 2/2006 |
| WO | WO 2007/003157 | | 1/2007 |
| WO | WO 2007/006516 | | 1/2007 |
| WO | WO 2007/006517 | | 1/2007 |
| WO | WO 2007/040702 | | 4/2007 |

OTHER PUBLICATIONS

510(k) Notification (21 CFR 807.90(e)) for the Plasma Surgical Ltd. PlasmaJet® Neutral Plasma Surgery System, Section 10—Executive Summary—K080197.

510(k) Summary, dated Jun. 2, 2008.

510(k) Summary, dated Oct. 30, 2003.

Aptekman, 2007, "Spectroscopic analysis of the PlasmaJet argon plasma with 5mm-0.5 coag-cut handpieces", Document PSSRP-106—K080197.

Asawanonda et al., 2000, "308-nm excimer laser for the treatment of psoriasis: a dose-response study." Arach. Dermatol. 136:619-24.

Branson, M.D., 2005, "Preliminary experience with neutral plasma, a new coagulation technology, in plastic surgery", Fayetteville, NY.

Charpentier et al., 2008, "Multicentric medical registry on the use of the Plasma Surgical PlasmaJet System in thoracic surgery", Club Thorax.

Chen et al., 2006, "What do we know about long laminar plasma jets?", Pure Appl Chem; 78(6):1253-1264.

Cheng et al., 2006, "Comparison of laminar and turbulent thermal plasma jet characteristics—a modeling study", Plasma Chem Plasma Process; 26:211-235.

Chinese Office Action (translation) of application No. 200680030225.5, dated Jun. 11, 2010.

Chinese Office Action (translation) of application No. 200680030216.6, dated Oct. 26, 2010.

Chinese Office Action (translation) of application No. 200680030194.3, dated Jan. 31, 2011.

Chinese Office Action (translation) of application No. 200680030225.5, dated Mar. 9, 2011.

CoagSafe™ Neutral Plasma Coagulator Operator Manual, Part No. OMC-2100-1, Revision 1.1, dated Mar. 2003—Appendix 1of K030819.

Coven et al., 1999, "PUVA-induced lymphocyte apoptosis: mechanism of action in psoriasis." Photodermatol. Photoimmunol. Photomed. 15:22-7.

Dabringhausen et al., 2002, "Determination of HID electrode falls in a model lamp I: Pyrometric measurements." J. Phys. D. Appl. Phys. 35:1621-1630.

Davis J.R. (ed) ASM Thermal Spray Society, Handbook of Thermal Spray Technology, 2004, U.S. 42-168.

Deb et al., "Histological quantification of the tissue damage caused in vivo by neutral PlasmaJet coagulator", Nottingham University Hospitals, Queen's medical Centre, Nottingham NG7 2UH—Poster.

Device drawings submitted pursuant to MPEP §724 in U.S. Appl. No. 11/482,582.

Electrosurgical Generators Force FX™ Electrosurgical Generators by ValleyLab—K080197.

ERBE APC 300 Argon Plasma Coagulation Unit for Endoscopic Applications, Brochure—Appendix 4 of K030819.

European Office Action of application No. 07786583.0-1226, dated Jun. 29, 2010.

Feldman et al., 2002, "Efficacy of the 308-nm excimer laser for treatment of psoriasis: results of a multicenter study." J. Am Acad. Dermatol. 46:900-6.

FORCE Argon™ II System, Improved precision and control in electrosurgery, by Valleylab—K080197.

Gerber et al., 2003, "Ultraviolet B 308-nm excimer laser treatment of psoriasis: a new phototherapeutic approach." Br. J. Dermatol. 149:1250-8.

Gugenheim et al., 2006, "Open, muliticentric, clinical evaluation of the technical efficacy, reliability, safety, and clinical tolerance of the plasma surgical PlasmaJet System for intra-operative coagulation in open and laparoscopic general surgery", Department of Digestive Surgery, University Hospital, Nice, France.
Haemmerich et al., 2003, "Hepatic radiofrequency ablation with internally cooled probes: effect of coolant temperature on lesion size", IEEE Transactions of Biomedical Engineering; 50(4):493-500.
Haines et al., "Argon neutral plasma energy for laparoscopy and open surgery recommended power settings and applications", Royal Surrey County Hosptial, Guildford Surrey, UK.
Honigsmann, 2001, "Phototherapy for psoriasis." Clin. Exp. Dermatol. 26:343-50.
Huang et al., 2008, "Laminar/turbulent plasma jets generated at reduced pressure", IEEE Transaction on Plasma Science; 36(4):1052-1053.
Iannelli et al., 2005, "Neutral plasma coagulation (NPC)—A preliminary report on a new technique for post-bariatric corrective abdominoplasty", Department of Digestive Surgery, University Hospital, Nice, France.
International Search Report of application No. PCT/EP2010/060641, dated Apr. 14, 2011.
International Preliminary Report on Patentability of International application No. PCT/EP2007/006939, dated Feb. 9, 2010.
International Preliminary Report on Patentability of International application No. PCT/EP2007/006940, dated Feb. 9, 2010.
International Search Report of International application No. PCT/EP2010/051130, dated Sep. 27, 2010.
International-type Search report dated Jan. 18, 2006, Swedish App. No. 0501604-3.
International-type Search report dated Jan. 18, 2006, Swedish App. No. 0501603-5.
International-type Search Report dated Jan. 18, 2006, Swedish App. No. 0501602-7.
Japanese Office Action (translation) of application No. 2008-519873, dated Jun. 10, 2011.
Japanese Office Action of application No. 2009-547536, dated Feb. 15, 2012.
Letter to FDA re: 501(k) Notification (21 CFR 807.90(e)) for the PlasmaJet® Neutral Plasma Surgery System, dated Jun. 2, 2008—K080197.
Lichtenberg et al., 2002, "Observation of different modes of cathodic arc attachment to HID electrodes in a model lamp." J. Phys. D. Appl. Phys. 35:1648-1656.
Marino, M.D., "A new option for patients facing liver resection surgery", Thomas Jefferson University Hospital.
McClurken et al., "Collagen shrinkage and vessel sealing", TissueLink Medical, Inc., Dover, NII; Technical Brief #300.
McClurken et al., "Histologic characteristics of the TissueLink Floating Ball device coagulation on porcine liver", TissueLink Medical, Inc., Dover, NH; Pre-Clinical Study #204.
Merloz, 2007, "Clinical evaluation of the Plasma Surgical PlasmaJet tissue sealing system in orthopedic surgery—Early report", Orthopedic Surgery Department, University Hospital, Grenoble, France.
News Release and Video—2009, New Sugical Technology Offers Better Outcomes for Women's Reproductive Disorders: Stanford First in Bay Area to Offer PlasmaJet, Stanford Hospital and Clinics.
Nezhat et al., 2009, "Use of neutral argon plasma in the laparoscopic treatment of endometriosis", Journal of the Society of Laparoendoscopic Surgeons.
Notice of Allowance and Fees Due, dated Oct. 28, 2011 of U.S. Appl. No. 11/482,581.
Notice of Allowance dated May 15, 2009, of U.S. Appl. No. 11/890,938.
Notice of Allowance of U.S. Appl. No. 12/557,645, dated May 26, 2011.
Notice of Allowance of U.S. Appl. No. 11/701,911, dated Dec. 6, 2010.
Office Action dated Apr. 17, 2008 of U.S. Appl. No. 11/701,911.
Office Action dated Feb. 1, 2008 of U.S. Appl. No. 11/482,580.
Office Action dated Mar. 13, 2009 of U.S. Appl. No. 11/701,911.
Office Action dated Mar. 19, 2009 of U.S. Appl. No. 11/482,580.
Office Action dated Oct. 18, 2007 of U.S. Appl. No. 11/701,911.
Office Action of U.S. Appl. No. 11/482,583, dated Oct. 18, 2009.
Office Action of U.S. Appl. No. 11/701,911, dated Sep. 29, 2009.
Office Action of U.S. Appl. No. 11/890,937, dated Sep. 17, 2009.
Office Action of U.S. Appl. No. 11/482,581, dated Dec. 8, 2010.
Office Action of U.S. Appl. No. 11/482,581, dated Jun. 24, 2010.
Office Action of U.S. Appl. No. 11/701,911 dated Apr. 2, 2010.
Office Action of U.S. Appl. No. 11/701,911 dated Jul. 19, 2010.
Office Action of U.S. Appl. No. 11/890,937 dated Apr. 9, 2010.
Office Action of U.S. Appl. No. 12/557,645, dated Nov. 26, 2010.
Palanker et al., 2008, "Electrosurgery with cellular precision", IEEE Transactions of Biomedical Engineering; 55(2):838-841.
Pan et al., 2001, "Generation of long, laminar plasma jets at atmospheric pressure and effects of low turbulence", Plasma Chem Plasma Process; 21(1):23-35.
Pan et al., 2002, "Characteristics of argon laminar DC Plasma Jet at atmospheric pressure", Plasma Chem and Plasma Proc; 22(2):271-283.
PCT International Preliminary Report on Patentability and Written Opinion of the International Searching Authority, dated Aug. 4, 2009 of International Application No. PCT/EP2007/000919.
PCT International Search Report dated Feb. 22, 2007, International App. No. PCT/EP2006/006689.
PCT International Search Report dated Feb. 22, 2007, International App. No. PCT/EP2006/006690.
PCT International Search Report PCT/EP2007/006939, dated May 26, 2008.
PCT International Search Report PCT/EP2007/006940.
PCT International Search Report, dated Jan. 16, 2007, International App. No. PCT/EP2006/006688.
PCT International Search Report, dated Oct. 23, 2007, International App. No. PCT/EP2007/000919.
PCT Invitation to Pay Additional Fees PCT/EP2007/006940, dated May 20, 2008.
PCT Written Opinion of the International Searching Authority PCT/EP2007/006939, dated May 26, 2008.
PCT Written Opinion of the International Searching Authority dated Feb. 14, 2007, International App. No. PCT/EP2006/006688.
PCT Written Opinion of the International Searching Authority dated Feb. 22, 2007, International App. No. PCT/EP2006/006689.
PCT Written Opinion of the International Searching Authority dated, dated Feb. 22, 2007, International App. No. PCT/EP2006/006690.
PCT Written Opinion of the International Searching Authority dated Oct. 23, 2007, International App. No. PCT/EP2007/000919.
PCT Written Opinion of the International Searching Authority PCT/EP2007/006940.
Plasma Surgery: A Patient Safety Solution (Study Guide 002).
Plasma Surgical Headlines Article: Atlanta, Feb. 2, 2010—"New Facilities Open in UK and US".
Plasma Surgical Headlines Article: Atlanta, Feb. 2, 2010—"PlasmaJet to be Featured in Live Case at Endometriosis 2010 in Milan, Italy".
Plasma Surgical Headlines Article: Chicago, Sep. 17, 2008—"PlasmaJet Named Innovation of the Year by the Society of Laparoendoscopic Surgeons".
PlasmaJet English Brochure.
PlasmaJet Neutral Plasma Coagulator Brochure mpb 2100—K080197.
PlasmaJet Neutral Plasma Coagulator Operator Manual, Part No. OMC-2100-1 (Revision 1.7, dated May 2004)—K030819.
PlasmaJet Operator Manual Part No. OMC-2130-EN (Revision 3.1/Draft) dated May 2008—K080197.
Premarket Notification 510(k) Submission, Plasma Surgical Ltd.—PlasmaJet™ (formerly CoagSafe™) Neutral Plasma Coagulator, Additional information provided in response to the e-mail request dated Jul. 14, 2004—K030819.
Premarket Notification 510(k) Submission, Plasma Surgical Ltd. CoagSafe™, Section 4 Device Description—K030819.
Premarket Notification 510(k) Submission, Plasma Surgical Ltd. CoagSafe™, Section 5 Substantial Equivalence K030819.
Premarket Notification 510(k) Submission, Plasma Surgical Ltd. PlasmaJet®, Section 11 Device Description—K080197.

Report on the comparative analysis of morphological changes in tissue from different organs after using the PlasmaJet version 3 (including cutting handpieces), Aug. 2007—K080197.
Schmitz & Riemann, 2002, "Analysis of the cathode region of atmospheric pressure discharges." J. Phys. D. Appl. Phys. 35:1727-1735.
Severtsev et al. 1997, "Polycystic liver disease: sclerotherapy, surgery and sealing of cysts with fibrin sealant", European Congress of the International Hepatobiliary Association, Hamburg, Germany Jun. 8-12; p. 259-263.
Severtsev et al., "Comparison of different equipment for final haemostasis of the wound surface of the liver following resection", Dept. of Surgery, Postgraduate and Research Centre, Medical Centre of the Directorate of Presidential Affairs of the Russian Federation, Moscow, Russia—K030819.
Sonoda et al., "Pathologic analysis of ex-vivo plasma energy tumor destruction in patients with ovarian or peritoneal cancer", Gynecology Service, Department of Surgery—Memorial Sloan-Kettering Cancer Center, New York, NY—Poster.
The Edge in Electrosurgery From Birtcher, Brochure—Appendix 4 of K030819.
The Valleylab FORCE GSU System, Brochure—Appendix 4 of K030819.
Treat, "A new thermal device for sealing and dividing blood vessels", Dept. of Surgery, Columbia University, New York, NY.
Trehan & Taylor, 2002, "Medium-dose 308-nm excimer laser for the treatment of psoriasis." J. Am. Acad. Dermatol. 47:701-8.
Video—Laparoscopic Management of Pelvic Endometriosis, by Ceana Nezhat, M.D.
Video—Tissue Coagulation, by Denis F. Branson, M.D.
Video—Tumor Destruction Using Plasma Surgery, by Douglas A. Levine, M.D.
White Paper—A Tissue Study using the PlasmaJet for coagulation: A tissue study comparing the PlasmaJet with argon enhanced electrosurgery and fluid coupled electrosurgery.
White Paper—Plasma Technology and its Clinical Application: An introduction to Plasma Surgery and the PlasmaJet—a new surgical tehnology.
Written Opinion of International application No. PCT/EP2010/051130, dated Sep. 27, 2010.
Written Opinion of International application No. PCT/EP2010/060641, dated Apr. 14, 2011.
www.plasmasurgical.com, as of Feb. 18, 2010.
Zenker, 2008, "Argon plasma coagulation", German Medical Science; 3(1):1-5.
Chinese Office Action of application No. 200780052471.5, dated May 25, 2012 (with English translation).
Chinese Office Action of application No. 200780100857.9, dated May 25, 2012 (with English translation).
Chinese Office Action of application No. 200780100857.9, dated Nov. 28, 2011 (with English translation).
Office Action of U.S. Appl. No. 11/482,580, dated Apr. 11, 2012.
Office Action of U.S. Appl. No. 13/358,934, dated Apr. 24, 2012.
Japanese Office Action of application No. 2010-519340, dated Mar. 13, 2012 (with translation).
Chinese Office Action of application No. 200780100858.3, dated Apr. 27, 2012 (with English translation).
Japanese Office Action of application No. 2010-519339, dated Apr. 3, 2012 (with English translation).
Notice of Allowance and Fees Due of U.S. Appl. No. 13/358,934, dated Sep. 5, 2012.
Chinese Office Action of Chinese application No. 200780100858.3, dated Aug. 29, 2012.
Office Action of U.S. Appl. No. 11/482,580, dated Oct. 24, 2012.
Chinese Office Action of Chinese application No. 2012220800745680, dated Nov. 13, 2012.
Office Action of U.S. Appl. No. 12/696,411, dated Dec. 5, 2012.
Chinese Office Action of Chinese application No. 200780052471.5, dated Dec. 5, 2012.
Office Action of U.S. Appl. No. 11/890,937, dated Apr. 3, 2013.

* cited by examiner

PLASMA-GENERATING DEVICE HAVING A THROTTLING PORTION

CLAIM OF PRIORITY

This application is a continuation of U.S. application Ser. No. 11/482,582 filed on Jul. 7, 2006, now U.S. Pat. No. 8,105,325 which claims priority of a Swedish Patent Application No. 0501602-7 filed on Jul. 8, 2005.

FIELD OF THE INVENTION

The present invention relates to a plasma-generating device, comprising an anode, a cathode and a plasma channel which in its longitudinal direction extends at least partly from a point located between the cathode and the anode and through the anode. The plasma channel has a throttling portion. The invention also relates to a plasma surgical device, use of such a plasma surgical device in surgery, and a method of generating plasma.

BACKGROUND ART

Plasma devices refer to devices configured for generating plasma. Such plasma can be used, for example, in surgery for destruction (dissection, vaporization) and/or coagulation of biological tissues.

As a general rule, such plasma devices have a long and narrow end that can be easily held and pointed toward a desired area to be treated, such as bleeding tissue. Plasma is discharged from a distal end. The high temperature of the discharged plasma allows for treatment of the affected tissue.

Owing to the recent developments in surgical technology, laparoscopic (keyhole) surgery is being used more often. Performing laparoscopic surgery requires devices with small dimensions to allow access to the surgical site without extensive incisions. Small instruments are also advantageous in any surgical operation for achieving good accuracy.

WO 2004/030551 (Suslov) discloses a prior-art plasma surgical device, which is intended for, among others, reducing bleeding in living tissue with plasma. This device comprises an anode, a cathode, and a gas supply channel for supplying plasma-generating gas to the device. Further, this plasma-generating device comprises at least one electrode arranged upstream of the anode. A housing connected to the anode, made of an electrically conductive material, encloses elements of the plasma-generating system and forms the gas supply channel.

It is desirable to provide a plasma-generating device capable of not only coagulation of bleeding living tissue, but also of cutting it.

With the device according to WO 2004/030551, generally a relatively high plasma-generating gas flow rate is required to generate a plasma flow capable of cutting. To generate a plasma flow with a suitable temperature at such flow rates, it is necessary to apply a relatively high operating electric current to the device.

It is desirable, however, to operate plasma-generating devices at relatively low operating electric currents, since high operating electric currents are often difficult to provide in certain environments, for example, in a medical environment. Also, as a general rule, a high operating electric current also requires extensive wiring, which can get unwieldy to handle during high precision procedures, for example, in laparoscopic surgery.

Alternatively, the device according to WO 2004/030551 could be formed with a relatively long plasma channel to generate a plasma flow with a suitable temperature at the required gas flow speeds. However, a longer plasma channel would make the device long and unwieldy for certain applications, for example, for medical applications, and especially for laparoscopic surgery.

For many applications, the generated plasma should be pure, i.e., have a low amount of impurities. It is also desirable that the discharged plasma flow has a pressure and a flow rate that are not harmful to a patient.

According to the above, there is a need for improved plasma-generating devices capable of effectively cutting biological tissue. The devices should be capable of being easily held and maneuvered. There is also a need for improved plasma-generating devices that can generate a pure plasma at lower operating currents and at lower gas flow rates.

SUMMARY OF THE INVENTION

An object of the present invention is to provide an improved plasma-generating device. Plasma is generated inside the device and is discharged from the distal end, also referred to as the discharge end. In general, the term “distal” refers to facing the discharge end of the device; the term “proximal” refers to facing the opposite direction. The terms “distal” and “proximal” can be used to describe the ends of the device and its elements. The flow of plasma gives meaning to the terms “upstream” and “downstream.”

Another object is to ensure that the device is useful in the field of the surgery.

A further object is to provide a method of generating plasma for cutting biological tissue.

According to one aspect of the invention, a plasma-generating device comprises an anode, a cathode, and an elongated plasma channel that has an inlet at a point between the cathode and the anode and an outlet at the distal end of the device. The plasma channel has a throttling portion arranged in it. The throttling portion divides the plasma channel into a high pressure chamber and a low pressure chamber. The high pressure chamber is located upstream of the throttling portion. The high pressure chamber has a first maximum cross-sectional area transverse to the longitudinal direction of the plasma channel opening into the anode. The low pressure chamber, downstream of the throttling portion, has a second maximum cross-sectional area transverse to the longitudinal direction of the plasma channel. (In the remainder of the disclosure, unless expressly stated otherwise, the term “cross-section” and its variations refer to a cross-section transverse to the longitudinal axis of the device.) The throttling portion has an hourglass shape. The throttling portion has a throat having a third cross-sectional area that is smaller than both the first maximum cross-sectional area and the second maximum cross-sectional area. At least one intermediate electrode is arranged between the cathode and the throttling portion. Preferably, the intermediate electrode can be arranged inside the high pressure chamber or form a part thereof.

This construction of the plasma-generating device allows plasma flowing in the plasma channel to be heated to a high temperature at a low operating current supplied to the plasma-generating device. In this disclosure, “high temperature” refers to a temperature above 11,000° C., preferably, above 13,000° C. The plasma flowing through the high pressure chamber is heated to a temperature between 11,000 and 20,000° C. In one embodiment, the plasma is heated to a temperature between 13,000 and 18,000° C. In another embodiment, the plasma is heated to a temperature between 14,000 and 16,000° C. In this disclosure, a “low operating current” means a current of below 10 Amperes. The operating current supplied to the device is preferably between 4 and 8 Amperes. With these operating currents, a supplied voltage is preferably between 50 and 150 volts.

Low operating currents are desirable in, for example, a surgical environment, where it can be difficult and not safe to provide the necessary supply of higher current levels. As a rule, high operating current levels require difficult to handle, extensive, unwieldy wiring, which is problematic for application requiring great accuracy, such as surgery, and in particular laparoscopic surgery. High operating currents can also be a safety risk for an operator and/or patient in certain environments and applications.

It is known that plasma suitable for biological tissue cutting can be obtained by designing the plasma channel in a suitable manner. The use of a throttling portion and a high pressure chamber, which allow heating of the plasma to desirable temperatures at preferred operating currents, provides the means for generating such plasma. Pressurizing the plasma in the high pressure chamber, upstream of the throttling portion, increases the energy density of the plasma. “Energy density” refers to the energy stored in a unit of plasma volume. Increased energy density is the result of the plasma, in the high pressure chamber, being heated by an electric arc established between the cathode and the anode in the plasma channel. The increased pressure in the high pressure chamber has also been found to enable operation of the plasma-generating device at lower operating currents. Furthermore, the increased pressure of the plasma in the high pressure chamber has also been found to enable operation of the device at lower plasma-generating gas flow rates. For example, experiments have shown that pressurization of the plasma in the high pressure chamber to about 6 bar can improve efficiency of the device by 30% compared to prior art devices, in which the plasma channel is arranged without a throttling portion and a high pressure chamber.

It has also been found that power loss in the anode can be reduced, compared with prior art plasma-generating devices, by pressurizing the plasma in a high pressure chamber.

It is also desirable to discharge plasma at a lower pressure than the pressure built up in the high pressure chamber. For example, the pressure built up in the high pressure chamber can be harmful to a patient. However, it has been found that the divergent portion of the throttling portion reduces the increased pressure of the plasma in the high pressure chamber as the plasma passes through it. (In this disclosure the term “pressure” refers to the static plasma flow pressure.) When passing the divergent portion, some of the excess pressure occurring in the high pressure chamber is converted into kinetic energy and the plasma flow is accelerated from the flow rate in the high pressure chamber.

A further advantage of the plasma-generating device according to the invention is that the plasma discharged through the plasma channel outlet has a higher kinetic energy than the kinetic energy of plasma flowing through the high pressure chamber. A plasma flow discharged with such an increased kinetic energy has been found suitable for cutting living biological tissue. Such a kinetic energy is sufficient for a plasma flow to penetrate an object and thus produce a cut.

It has also been found preferable, for surgical applications, to supply to the device a plasma-generating gas at a relatively low flow rate because a relatively high flow rate can be harmful to the treated patient. With low flow rates of the plasma-generating gas supplied to the device, it has been found that there exists the risk of one or more electric arcs forming between the cathode and walls of the high pressure chamber. This phenomenon is known as cascade electric arcs.

It has also been found that the possibility of such cascade electric arcs occurrence increases with a reduced cross-section of the plasma channel. Such cascade electric arcs can have a detrimental effect on the function of the plasma device, and the elements forming the high pressure chamber can be damaged and/or degraded as a result of the cascade electric arcs. There is also the risk that substances released from elements forming the high pressure chamber, as a result of the cascade electric arcs, would contaminate plasma, which can be harmful to a patient. Experiments have shown that the above-noted problems can arise with a gas flow rate of less than 1.5 l/min and a cross-section of the plasma channel of less than 1 $mm^2$.

In one aspect of the invention, it is preferable to arrange at least one intermediate electrode in the high pressure chamber to reduce the risk of the cascade electric arcs occurrence. Preferably, the cross-section of the high pressure chamber, formed by at least one intermediate electrode, is selected so that the desired temperature of the electric arc, and thus the desired temperature of plasma, can are achieved at the above operating current levels. The arrangement of at least one intermediate electrode forming the high pressure chamber reduces the risk of the plasma contamination. In the high pressure chamber formed by the intermediate electrode(s), the electric arc heats the generated plasma. Intermediate electrodes refer to one or more electrodes arranged upstream of the anode. It should also be appreciated that electric voltage is applied across each intermediate electrode during operation of the plasma-generating device.

In the preferred embodiment, the plasma-generating device comprises at least one intermediate electrode arranged upstream of the throttling portion and forming the high pressure chamber with a relatively small cross-section. Such a device is capable of generating plasma with unexpectedly low contamination levels and other desirable properties, which are particularly useful for cutting biological tissue. However, it is noted that the plasma-generating device can also be used for other surgical applications. It is possible to generate plasma suitable for vaporization or coagulation of biological tissue by changing current and/or gas flow rates.

It has also been found that the plasma-generating device allows controlled variations of the relationship between thermal energy and kinetic energy of the generated plasma. It has been found convenient to be able to use plasma with different relationships between thermal energy and kinetic energy when treating different objects, such as soft and hard biological tissue. It has also been found convenient to vary the relationship between thermal energy and kinetic energy depending on the blood flow rate in the biological tissue that is to be treated. In some cases it is convenient to use a plasma with a greater amount of thermal energy in connection with higher blood flow rate in the tissue and a plasma with lower thermal energy in connection with lower blood flow rate in the tissue. The relationship between thermal energy and kinetic energy of the generated plasma can be controlled, for example, by the pressure level established in the high pressure chamber. Higher pressure in the high pressure chamber results in the increased kinetic energy of the plasma flow when it is being discharged. Consequently, the ability to vary the relationship between thermal energy and kinetic energy of the generated plasma permits the combination of the cutting action and the coagulating action to be adjusted for treatment of different types of biological tissue, in surgical applications.

Preferably, the high pressure chamber is formed mainly of the one or more intermediate electrodes. In the high pressure chamber formed by the intermediate electrode(s), the electric arc effectively heats the passing plasma. Having the intermediate electrode(s) form a part of the high pressure chamber provides an advantage of the high pressure chamber being of a suitable length without the cascade electric arcs forming between the cathode and the inside surface of these electrode (s). As mentioned above, an electric arc formed between the cathode and the inner surface of an intermediate electrode can damage and/or degrade the high pressure chamber.

In one embodiment of the plasma-generating device, the high pressure chamber is formed by two or more intermediate electrodes. In that embodiment, the plasma channel is formed by multielectrodes. By forming the high pressure chamber by multielectrodes, the high pressure chamber can be given an increased length to allow the plasma to be heated to about the temperature of the electric arc. The smaller cross-section and the larger length of the high pressure chamber have been found necessary for heating the plasma to about the temperature of the electric arc. Experiments focusing on the length of the intermediate electrodes forming the plasma channel have been performed. The experiments have shown that a higher number of intermediate electrodes can be used to decrease the length of each electrode forming the plasma channel. Increasing the number of the intermediate electrodes results in reduction of the applied electric voltage across each intermediate electrode.

It has also been found beneficial to arrange a larger number of intermediate electrodes downstream of the throttling portion when increasing the pressure of the plasma in the high pressure chamber. In addition, it has been observed that by using a larger number of intermediate electrodes when increasing the pressure of the plasma in the high pressure chamber, it is possible to maintain substantially the same voltage differential per intermediate electrode, which reduces the risk of the cascade electric arcs occurrence.

The use of a relatively long high pressure chamber demonstrates the risk that the electric arc does not get established between the cathode and the anode if each individual electrode is too long. Instead, shorter electric arcs are established between the cathode and the intermediate electrodes and/or between adjacent intermediate electrodes. Preferably, a relatively high number of intermediate electrodes form the high pressure chamber and, thus, reducing the voltage applied to each intermediate electrode. Consequently, a relatively high number of intermediate electrodes should be used when forming a long high pressure chamber, especially when the high pressure chamber has a small cross-sectional area. Experiments have shown that the voltage of less than 22 volt can be safely applied to each of the intermediate electrodes. With preferred operating current levels as stated above, it has been found that the voltage level across the electrodes is preferably between 15 and 22 volt/mm.

In one embodiment, the high pressure chamber is formed by three or more intermediate electrodes as a part of a multi-electrode plasma channel.

In one embodiment of the plasma-generating device, the second maximum cross-sectional area is equal to or is smaller than 0.65 $mm^2$. In one embodiment, the second maximum cross-sectional area is between 0.05 and 0.44 $mm^2$. In an alternative embodiment, the second maximum cross-sectional area is between 0.13 and 0.28 $mm^2$. By arranging the low pressure chamber with such cross-sectional areas, it has been found possible to discharge, through the plasma channel outlet, a plasma flow with high energy concentration. A plasma flow with high energy concentration is particularly useful for cutting biological tissue. A small cross-sectional area of the generated plasma flow is also advantageous for procedures requiring a great accuracy. Moreover, a low pressure chamber with such cross-sections facilitates plasma acceleration, increase in kinetic energy, and reduction in pressure, making the plasma suitable for use in surgical applications.

The third cross-sectional area is preferably in the range between 0.008 and 0.12 $mm^2$. In an alternative embodiment, the third cross sectional area is between 0.030 and 0.070 $mm^2$. The throttling portion with the throat having such a cross-sectional area has been found to produce an optimal pressure increase of plasma in the high pressure chamber. Furthermore pressurization of the plasma in the high pressure chamber affects plasma's energy density as described above. The pressure increase of plasma in the high pressure chamber by the throttling portion is thus advantageous to obtain desirable heating of the plasma at preferred plasma-generating gas flow rates and operating current levels.

The selected cross-sectional area of the throttling portion throat results in the pressure, in the high pressure chamber, that is capable of accelerating the plasma flow to a supersonic speed with a value equal to or greater than Mach 1, when the plasma passes through the throttling portion. The critical pressure level required in the high pressure chamber for the plasma flow to achieve supersonic speeds in the low pressure chamber has been found to depend on, among others, the cross-sectional area of the throat and the geometric shape of the throttling portion. It has also been found that the critical pressure for achieving supersonic speeds is also dependent on the kind of plasma-generating gas used and the plasma temperature. It should be noted that the third cross sectional area (of the throttling portion throat) is always smaller than the first maximum (of the high pressure chamber) and the second (of the low pressure chamber) maximum cross-sectional areas.

Preferably, the first maximum cross-sectional area of the high pressure chamber is in the range between 0.03 and 0.65 $mm^2$. Such a maximum cross-sectional area has been found suitable for heating the plasma to the desired temperature at the preferred levels of gas flow rates and operating currents.

The temperature of an electric arc established between the cathode and the anode depends on, among others, the first maximum cross-sectional area of the high pressure chamber. A smaller cross-sectional area of the high pressure chamber results in the increased energy density of the electric arc. The temperature of the electric arc along the center axis of the plasma channel is proportional to the quotient of the discharge current (passing between the cathode and the anode) and the cross-sectional area of the plasma channel.

In an alternative embodiment, the high pressure chamber has the first cross-sectional area of between 0.05 and 0.33 $mm^2$. In another alternative embodiment, the high pressure chamber has the first cross-sectional area between 0.07 and 0.20 $mm^2$.

Preferably, the throttling portion is formed by an intermediate electrode. This arrangement reduces the risk of the cascade electric arcs occurring between the cathode and the throttling portion. Similarly, this arrangement decreases the risk of the cascade electric arcs occurring between the throttling portion and other intermediate electrodes, such as electrodes adjacent to the throttling portion.

Preferably, the low pressure chamber is formed by at least one intermediate electrode. Forming the low pressure chamber with one or more intermediate electrodes reduces the risk of the cascade electric arcs occurring between the cathode and the surface of the low pressure chamber. This also reduces the risk of the cascade electric arc occurring between neighboring intermediate electrodes.

Preferably, the intermediate electrodes forming the throttling portion and the low pressure chamber contribute to the properly established electric arc between the cathode and the anode. For some applications it may be desirable to arrange the throttling portion between two intermediate electrodes, one forming the high pressure chamber and another forming the low pressure chamber. In one embodiment, the throttling portion can be arranged between (1) at least two intermediate electrodes that form a part of the high pressure chamber and (2) at least two intermediate electrodes that form a part of the low pressure chamber.

It has been found suitable to design the plasma-generating device in such a manner that a substantial part of the plasma channel that extends from a point between the cathode and the anode to the anode is formed by intermediate electrodes. Such a channel also makes possible heating of plasma along substantially the entire length of the plasma channel.

In one embodiment, the plasma-generating device comprises at least two intermediate electrodes, preferably at least three intermediate electrodes. In an alternative embodiment, the plasma-generating device comprises between 2 and 10 intermediate electrodes, and according to another alternative embodiment between 3 and 10 intermediate electrodes. Varying the number of intermediate electrodes allows forming the plasma channel of an optimal length for heating plasma at desirable levels of the plasma-generating gas flow rate and operating current. Moreover, the intermediate electrodes are preferably spaced from each other with insulator washers. The intermediate electrodes are preferably made of copper or alloys containing copper.

In one embodiment, the first maximum cross-sectional area, the second maximum cross-sectional area, and the third cross-sectional area are circles. Circular cross-sections of the plasma channel simplify and make less expensive the manufacture of the device.

In one embodiment, the distal portion of the cathode has a tip tapering toward the anode. Further in one embodiment, an intermediate electrode forms a plasma chamber connected to the inlet of the plasma channel. A part of the cathode tip extends over a partial length of the plasma chamber. The plasma chamber has a fourth cross-sectional area that is larger than the first maximum cross-sectional area. Such a plasma chamber makes it possible to reduce the plasma-generating device's outer dimensions. The plasma chamber provides space around the distal end of the cathode, especially the tip. This space reduces the risk that, in operation, the heat emanating from the cathode would damage and/or degrade elements in the proximity of the cathode. The plasma chamber is particularly important for long continuous periods of the device operation.

Another advantage is achieved by the plasma chamber in the proper generation of the electric arc. Specifically, for proper operation, the electric arc must be established between the cathode and the anode. For that to happen, the initial spark must enter into the plasma channel. The plasma chamber allows the tip of the cathode to be positioned in the vicinity of the plasma channel inlet without the surrounding elements being damaged and/or degraded due to the high temperature of the cathode. If the tip of the cathode is positioned at too great a distance from the plasma channel inlet, an electric arc is often established between the cathode and another structure, which may result in incorrect operation of the device and in some cases even in the device being damaged.

According to a second aspect of the invention, a plasma surgical device, comprising a plasma-generating device as described above, is provided. Such a plasma surgical device can be used for destruction or coagulation of biological tissue, and especially for cutting. Moreover, such a plasma surgical device can be used in heart or brain surgery. Alternatively, such a plasma surgical device can be used in liver, spleen, or kidney surgery.

According to a third aspect of the invention, a method of generating plasma is provided. This method comprises, at an operating current of 4 to 10 Amperes, supplying to the plasma-generating device a plasma-generating gas at the flow rate of 0.05 to 1.00 l/min. The plasma-generating gas preferably comprises an inert gas, such as argon, neon, xenon, helium etc. This method produces a plasma flow suitable for cutting biological tissue.

In an alternative embodiment, the flow rate of the supplied plasma-generating gas can be between 0.10 and 0.80 l/min. In another alternative embodiment, the flow rate can be between 0.15 and 0.50 l/min.

According to a fourth aspect of the invention, a method of generating plasma by a plasma-generating device is provided. The device comprises an anode, a cathode, and a plasma channel extending from a point between the cathode and the anode and through the anode, the plasma channel having a throttling portion. The method comprises providing plasma flowing from the cathode to the anode (this direction of the plasma flow gives meaning to the terms “upstream” and “downstream” as used herein); increasing energy density of the plasma flow by pressurizing plasma in a high pressure chamber positioned upstream of the throttling portion; heating the plasma by using at least one intermediate electrode which is arranged upstream of the throttling portion; and depressurizing and accelerating the plasma flow by passing it through the throttling portion and discharging the plasma flow through the plasma channel outlet.

With such a method, it is possible to generate a substantially contaminant free plasma flow that can be heated to the desired temperature and be given the desired kinetic energy at the operating currents and gas flow levels as described above.

The pressure of plasma in the high pressure chamber is between 3 and 8 bar, preferably 5-6 bar. Such pressure levels are preferred for providing the plasma flow with energy density that facilitates heating to desirable temperatures at desirable operating current levels. Such pressure levels have also been found to result in acceleration of the plasma flow to a supersonic speed when the flow passes through the throttling portion.

In the low pressure portion, the plasma flow is preferably pressurized to a level that exceeds the prevailing atmospheric pressure outside the plasma channel outlet by less than 2 bar, alternatively 0.25-1 bar, and according to another alternative 0.5-1 bar. Reducing the pressure of the plasma flow discharged from the plasma channel outlet to the above levels reduces the risk of the plasma flow injuring the treated patient.

As mentioned above, the increased pressure of the plasma flow in the high pressure chamber enables the plasma flow to accelerate to supersonic speed of Mach 1 or higher, when the plasma flow passes through the throttling portion. The pressure required to achieve a speed higher than Mach 1 depends on the pressure of the plasma flow and the nature of the supplied plasma-generating gas. The pressure in the high pressure chamber depends, in turn, on the shape of the throttling portion and the cross-sectional area of the throat. Preferably, the plasma flow is accelerated to 1-3 times the supersonic speed, that is the flow speed between Mach 1 and Mach 3.

Inside the plasma channel, in some embodiments the plasma is preferably heated to a temperature between 11,000 and 20,000° C., in other embodiments 13,000 to 18,000° C., and 14,000 to 16,000° C. Such temperature levels are sufficient to make the discharged plasma flow suitable for cutting biological tissue.

To generate and discharge the plasma flow, as described above, a plasma-generating gas is supplied to the plasma-generating device. It has been found preferable to provide the plasma-generating gas at the rate between 0.05 and 1.00 l/min, in other embodiments 0.10-0.80 l/min, and in the preferred embodiments, 0.15-0.50 l/min. With such flow rates of the plasma-generating gas, it is possible for plasma to be heated to the desired temperatures at desired operating current levels. The above-mentioned flow rates are also suitable in surgical applications because they do not create significant risk of injuries to a patient.

The plasma flow should be discharged through an outlet with a certain cross-sectional area. In some embodiments a cross-sectional area is below 0.65 $mm^2$, in some embodiments between 0.05 and 0.44 $mm^2$, and in the preferred embodiments 0.13-0.28 $mm^2$. In some embodiments the operating current is between 4 and 10 Amperes, preferably 4-8 Amperes is supplied to the device.

According to another aspect of the invention, the above-mentioned method of generating a plasma flow can be used as a part of a method for cutting biological tissue.

BRIEF DESCRIPTION OF THE DRAWINGS

The invention will now be described in more detail with reference to the accompanying schematic drawings, which by way of example illustrate currently preferred embodiments of the invention.

DESCRIPTION OF PREFERRED EMBODIMENTS

Figure 1A:
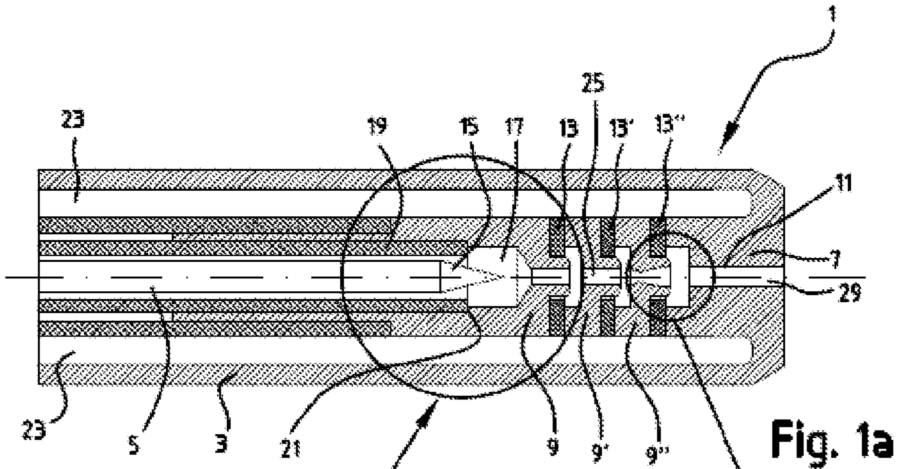
FIG. 1*a* is a longitudinal cross-sectional view of an embodiment of a plasma-generating device according to the invention.

FIG. 1*a* is a longitudinal cross-sectional view of one embodiment of a plasma-generating device 1 according to the invention. The cross-section in FIG. 1*a* is taken through the center of the plasma-generating device 1 in its longitudinal direction. The device comprises an elongated end sleeve 3 that encloses other elements of the device. In operation, plasma flows from the proximal end of the device (left side of FIG. 1*a*) and is discharged at the end of sleeve 3 (right side of FIG. 1*a*). The flow of plasma gives meaning to the terms "upstream" and "downstream." The discharge end of sleeve 3 is also referred to as the distal end of device 1. In general, the term "distal" refers to facing the discharge end of the device; the term "proximal" refers to facing the opposite direction. The terms "distal" and "proximal" can be used to describe the ends of device 1, as well as its elements. The generated plasma can be used, for example, to stop bleeding in tissues, vaporize tissues, cut tissues, etc.

The plasma-generating device 1 according to FIG. 1*a* comprises cathode 5, anode 7 and a number of electrodes 9, 9', 9", referred to as intermediate electrodes in this disclosure, arranged upstream of anode 7. In the preferred embodiment, the intermediate electrodes 9, 9', 9" are annular and form a part of a plasma channel 11, which extends from a position downstream of the cathode 5 and further toward and through anode 7. Plasma channel 11 extends through anode 7, where its outlet is arranged. In plasma channel 11, plasma is heated and discharged through the outlet. Intermediate electrodes 9, 9', 9" are insulated and separated from each other by an annular insulator washers 13, 13', 13". The shape of intermediate electrodes 9, 9',9" and the dimensions of the plasma channel 11 can be adjusted for any desired purpose. The number of intermediate electrodes 9, 9', 9" can also be varied. The exemplary embodiment shown in FIG. 1*a* is configured with three intermediate electrodes 9, 9', 9".

In the embodiment shown in FIG. 1*a*, cathode 5 is formed as an elongated cylindrical element. Preferably, cathode 5 is made of tungsten, optionally with additives, such as lanthanum. Such additives can be used, for example, to lower the temperature that the distal end of cathode 5 reaches.

In the preferred embodiment, the distal portion of cathode 5 has a tapering portion 15. Tapering portion 15 forms a tip as shown in FIG. 1*a*. Preferably, cathode tip 15 is a cone. In some embodiments, cathode tip 15 is a truncated cone. In other embodiments, cathode tip 15 may have other shapes, tapering toward anode 7.

The proximal end of cathode 5 is connected to an electrical conductor that is connected to an electric energy source. The conductor, which is not shown in FIG. 1*a*, is preferably surrounded by an insulator.

Plasma chamber 17 is connected to the inlet of plasma channel 11. Plasma chamber 17 has a cross-sectional area that is greater than the maximum cross-sectional area of plasma channel 11 at its inlet. Plasma chamber 17, as shown in FIG. 1*a*, has a circular cross-section and has length $L_{ch}$, which approximately equals diameter $D_{ch}$ of plasma chamber 17. Plasma chamber 17 and plasma channel 11 are substantially concentrically arranged relative to each other. In the preferred embodiment, cathode 5 is arranged substantially concentrically with plasma chamber 17. Cathode 5 extends into the plasma chamber 17 over approximately half of the plasma chamber 17's length. Plasma chamber 17 is formed by a recess in the proximal-most intermediate electrode 9.

FIG. 1*a* also shows insulator sleeve 19 extending along and around a portion of cathode 5. Cathode 5 is arranged substantially in the center of the through hole of insulator sleeve 19. The inner diameter of insulator sleeve 19 is slightly greater than the outer diameter of cathode 5. The difference in these diameters results in a gap formed by the outer surface of cathode 5 and the inner surface of insulator sleeve 19.

Preferably insulator sleeve 19 is made of a temperature-resistant material, such as ceramic, temperature-resistant plastic, or the like. Insulator sleeve 19 protects constituent elements of plasma-generating device 1 from heat generated by cathode 5, and in particular by cathode tip 15, during operation.

Insulator sleeve 19 and cathode 5 are arranged relative to each other so that the distal end of cathode 5 projects beyond the distal end of insulator sleeve 19. In the embodiment shown in FIG. 1*a*, approximately half of the length of cathode tip 15 extends beyond distal end 21 of insulator sleeve 19, which, in that embodiment, is a surface.

A gas supply part (not shown in FIG. 1*a*) is connected to the plasma-generating device. The gas supplied, under pressure, to plasma-generating device 1 consists of the same type of gases that are used in prior art instruments, for example, inert gases, such as argon, neon, xenon, or helium. The plasma-generating gas flows through the gas supply part and into the gap formed by the outside surface of cathode 5 and the inside surface of insulator sleeve 19. The plasma-generating gas flows along cathode 5 inside insulator sleeve 19 toward anode 7. (As mentioned above, this direction of the plasma flow gives meaning to the terms "upstream" and "downstream" as used herein.) As the plasma-generating gas passes distal end 21 of the insulator sleeve 19, the gas enters into plasma chamber 17.

The plasma-generating device 1 further comprises one or more auxiliary channels 23. Auxiliary channels 23 traverse a substantial length of device 1. In some embodiments, a proximal portion of each channel 23 is formed, in part, by a housing (not shown) which is connected to end sleeve 3, while a distal portion of each channel 23 is formed, in part, by end sleeve 3. End sleeve 3 and the housing can be interconnected by a threaded joint or by other coupling means, such as welding, soldering, etc. Preferably end sleeve 3 has a relatively small outer diameter, such as less than 10 mm, or, preferably, even less than 5 mm. The housing portion positioned at the proximal end of sleeve 3 has an outer shape and dimension that substantially correspond to the outer shape and dimension of sleeve 3. In the embodiment of the plasma-generating device shown in FIG. 1*a*, end sleeve 3 is circular in cross-section.

In one embodiment, plasma-generating device 1 has two channels 23 connecting inside end sleeve 3 in the vicinity of anode 7. In this configuration, channels 23 collectively form a cooling system with one channel 23 having an inlet and the other channel 23 having an outlet. The two channels are connected with each other to allow the coolant to pass between them inside end sleeve 3. It is also possible to arrange more than two channels 23 in the plasma-generating device 1. Preferably, water is used as coolant, although other fluids are contemplated. The cooling channels are arranged so that the coolant is supplied to end sleeve 3 and flows between intermediate electrodes 9, 9', 9" and the inner wall of end sleeve 3.

Intermediate electrodes 9, 9', 9" and insulator washers 13, 13', and 13" are arranged inside end sleeve 3 of the plasma-generating device 1 and are positioned substantially concentrically with end sleeve 3. The intermediate electrodes 9, 9', 9" and insulator washers 13, 13', and 13" have outer surfaces, which together with the inner surface of sleeve 3 form auxiliary channels 23.

The number and cross-section of auxiliary channels 23 can vary. It is also possible to use all, or some, of auxiliary channels 23 for other purposes. For example, three auxiliary channels 23 can be arranged, with two of them being used for cooling, as described above, and the third one being used for removing undesired liquids or debris from the surgical site.

In the embodiment shown in FIG. 1*a*, three intermediate electrodes 9, 9', 9" are spaced apart by insulator washers 13, 13', 13" arranged between each pair of the intermediate electrodes, and between the distal-most intermediate electrode and anode 7. The first intermediate electrode 9, the first insulator 13' and the second intermediate electrode 9' are press-fitted to each other.

The proximal-most electrode 9" is in contact with annular insulator washer 13", which, in turn, is in contact with anode 7. While in the preferred embodiment insulators 13, 13', and 13" are washers, in other embodiments they can have any annular shape.

Anode 7 is connected to elongated end sleeve 3. In the embodiment shown in FIG. 1*a*, anode 7 and end sleeve 3 are formed integrally with each other. Note that in this configuration, "anode" refers to the portion of the joint structure that forms a part of the plasma channel. In alternative embodiments, anode 7 can be formed as a separate element coupled to end sleeve 3 by any known means, such as a threaded joint, welding, or soldering. The connection between anode 7 and end sleeve 3 provides electrical contact between them.

Plasma-generating device 1 shown in FIG. 1*a* has plasma channel 11 which comprises high pressure chamber 25, throttling portion 27, and low pressure chamber 29. Throttling portion 27, which generally has an hourglass shape, is positioned between high pressure chamber 25 and low pressure chamber 29. In this disclosure, high pressure chamber 25 refers to the part of the plasma chamber 11 positioned upstream of throttling portion 27. Low pressure chamber 29 refers to the part of plasma channel 11 positioned downstream of the throttling portion 27.

Figure 1C:
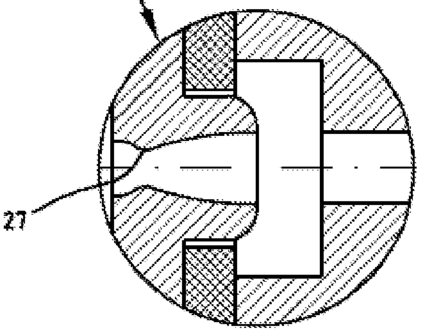
FIG. 1*c* is a partial enlargement of a throttling portion arranged in a plasma channel of the plasma-generating device in FIG. 1*a;*

Throttling portion 27 shown in FIG. 1*a* has a throat, which constitutes the smallest cross-section of the plasma channel 11. Consequently, the cross-section of the throttling portion throat is smaller than the maximum cross-section of high pressure chamber 25 and the maximum cross-section of low pressure chamber 29. As shown in FIGS. 1*a* and 1*c*, the throttling portion is preferably a supersonic nozzle or a de Laval nozzle.

In operation, throttling portion 27 results in the pressure of plasma in high pressure chamber 25 being greater than in low pressure chamber 29. When plasma flows through throttling portion 27, the plasma flow speed is increased and the pressure of the plasma flow drops. Consequently, the plasma flow discharged through the plasma channel outlet has a higher kinetic energy and a lower pressure than plasma in high pressure chamber 25. In the plasma-generating device shown in FIG. 1*a*, the outlet of the plasma channel 11 in anode 7 has the same cross-sectional area as the maximum cross-sectional area of low pressure chamber 29.

In the embodiment shown in FIG. 1*a*, as viewed in the direction of the plasma flow, the throttling portion 27 gradually converges toward the throat and gradually diverges from the throat. This shape of throttling portion 27, among others, reduces turbulence in the plasma flow. This is desirable because turbulence may reduce the plasma flow speed.

In the partial enlargement shown in FIG. 1*c*, throttling portion 27 converges upstream of the throat and diverges downstream of the throat. In the embodiment shown in FIG. 1*c*, the diverging portion is shorter than the converging portion.

With the design of the throttling portion 27, shown in FIG. 1*c*, it has been found possible to accelerate the plasma flow to a supersonic speed of Mach 1 or above.

Plasma channel 11 shown in FIG. 1*a* is circular in cross-section. High pressure chamber 25 has a maximum cross-sectional diameter between 0.20 and 0.90 mm; in some embodiments it is between 0.25 and 0.65 mm; and in the preferred embodiment it is between 0.30-0.50 mm. Moreover, low pressure chamber 29 has a maximum cross-sectional diameter between 0.20 and 0.90 mm; in some embodiments it is between 0.25 and 0.75 mm; and in the preferred embodiment it is between 0.40 and 0.60 mm. The throat of throttling portion 27 has a cross-sectional diameter between 0.10 and 0.40 mm, preferably between 0.20-0.30 mm.

FIG. 1*a* shows an exemplary embodiment of plasma-generating device 1 with high pressure chamber 25 having a cross-sectional diameter of 0.4 mm, low pressure chamber 29 having a cross-sectional diameter of 0.50 mm, and the throat of throttling portion 27 having a cross-sectional diameter of 0.27 mm.

In the embodiment shown in FIG. 1*a*, throttling portion 27 is positioned approximately in the middle of plasma channel 11. By changing the location of throttling portion 27 in plasma channel 11, it is possible, however, to vary the relationship between kinetic energy and thermal energy of the generated plasma flow.

Figure 2:
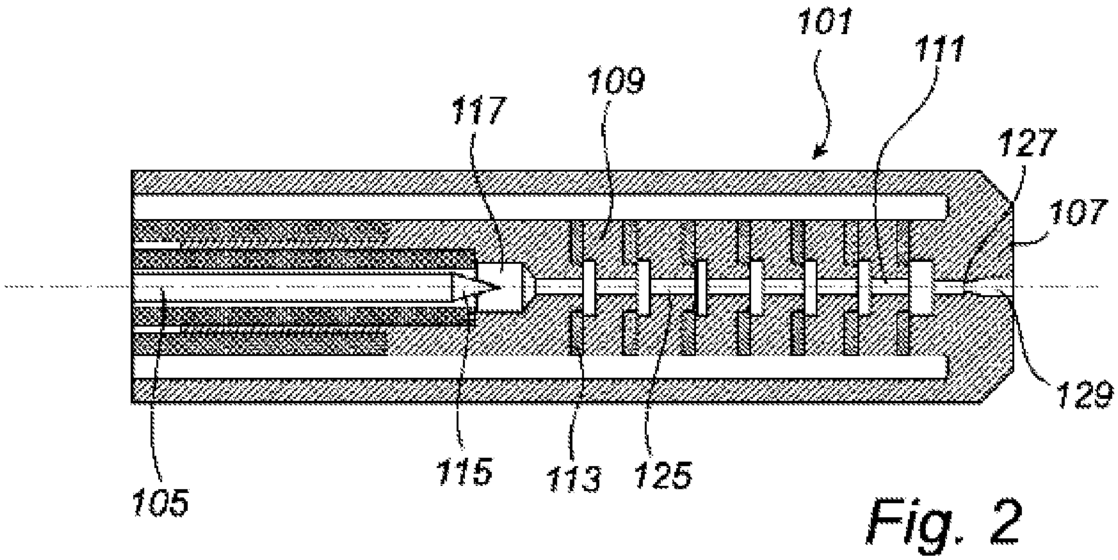
FIG. 2 illustrates an alternative embodiment of a plasma-generating device.

FIG. 2 is a cross-sectional view of an alternative embodiment of plasma-generating device 101. In the embodiment shown in FIG. 2, throttling portion 127 is formed by anode 107 in the vicinity of the plasma channel 111 outlet. By arranging throttling portion 127 in the distal portion of plasma channel 111, for example, in or near anode 107, it is possible to generate and discharge a plasma flow with a higher kinetic energy compared with the embodiment of device 1 shown in FIG. 1*a*. It has been found that certain types of tissue, for example, soft tissues such as liver, can be cut easier with a plasma flow having a higher kinetic energy. Specifically, it has been found preferable for the plasma flow used for cutting such tissues to have approximately 50% of its energy be thermal and approximately 50% be kinetic.

The embodiment of plasma-generating device 101 in FIG. 2 comprises seven intermediate electrodes 109. It will be appreciated, however, that the embodiment of the plasma-generating device 101 in FIG. 2 can have more or fewer than seven intermediate electrodes 109.

Figure 3:
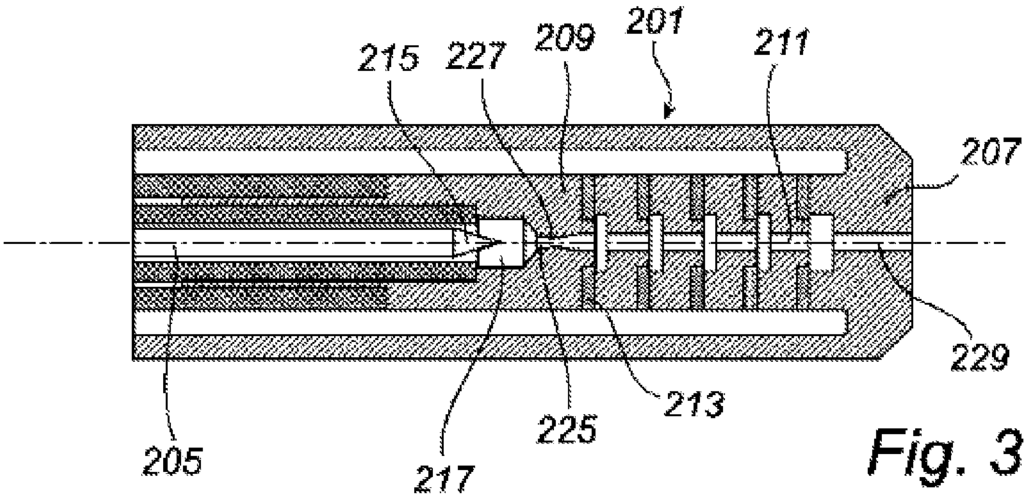
FIG. 3 illustrates another alternative embodiment of a plasma-generating device.

FIG. 3 shows another alternative embodiment of plasma-generating device 201. In the embodiment shown in FIG. 3, throttling portion 227 is formed by the proximal-most intermediate electrode 209. By arranging throttling portion 227 in the proximal portion of plasma channel 211, it is possible to generate and discharge a plasma flow with lower kinetic energy compared with embodiments of devices 1 and 101 shown in FIGS. 1*a*. and 2, respectively. It has been found that certain hard tissues, such as bone, can be cut easier with a plasma flow having higher thermal energy and lower kinetic energy. For example, it has been found preferable for bone cutting to generate a plasma flow with 80-90% of the total energy being thermal and 10-20% of the total energy being kinetic.

The embodiment of the plasma-generating device 201 in FIG. 3 comprises five intermediate electrodes 209. It will be appreciated, however, that the embodiment of the plasma-generating device 201 in FIG. 3 can have more or fewer than five intermediate electrodes 209.

It will be appreciated that depending on the desired properties of the discharged plasma flow, the throttling portion can be arranged in practically any position in the plasma channel. Moreover, it will be appreciated that alternative arrangements of elements described with reference to the embodiment shown in FIGS. 1*a*-1*c*, similarly apply to the embodiments shown in FIGS. 2-3, as well as other embodiments.

Figure 4:
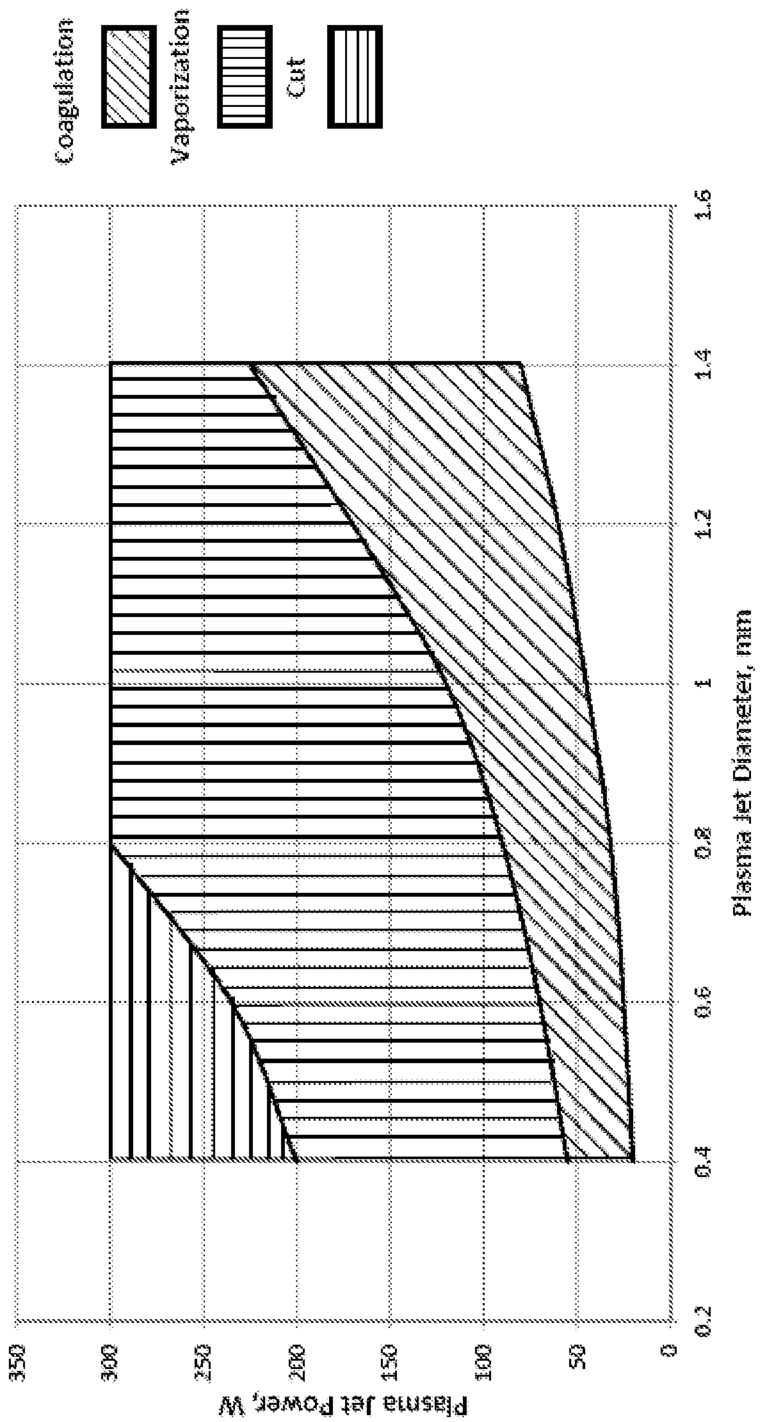
FIG. 4 shows exemplary power levels to affect biological tissue in different ways.

FIG. 4 shows power levels of a plasma flow for achieving different effects (i.e., coagulation, vaporization, or cutting) on an exemplary living biological tissue. It is apparent that the same effect can be achieved at different power levels depending on the diameter of the discharged plasma flow. FIG. 4 shows the relationships between these power levels and the diameter of plasma flows discharged from plasma channel 1; 111; or 211 of respective devices 1; 101; 201, as described above. To reduce the operating current, it has been found preferable to reduce the diameter of plasma channel 11; 111; 211, and consequently reduce the diameter of the discharged plasma flow, as shown in FIG. 4.

Figure 5:
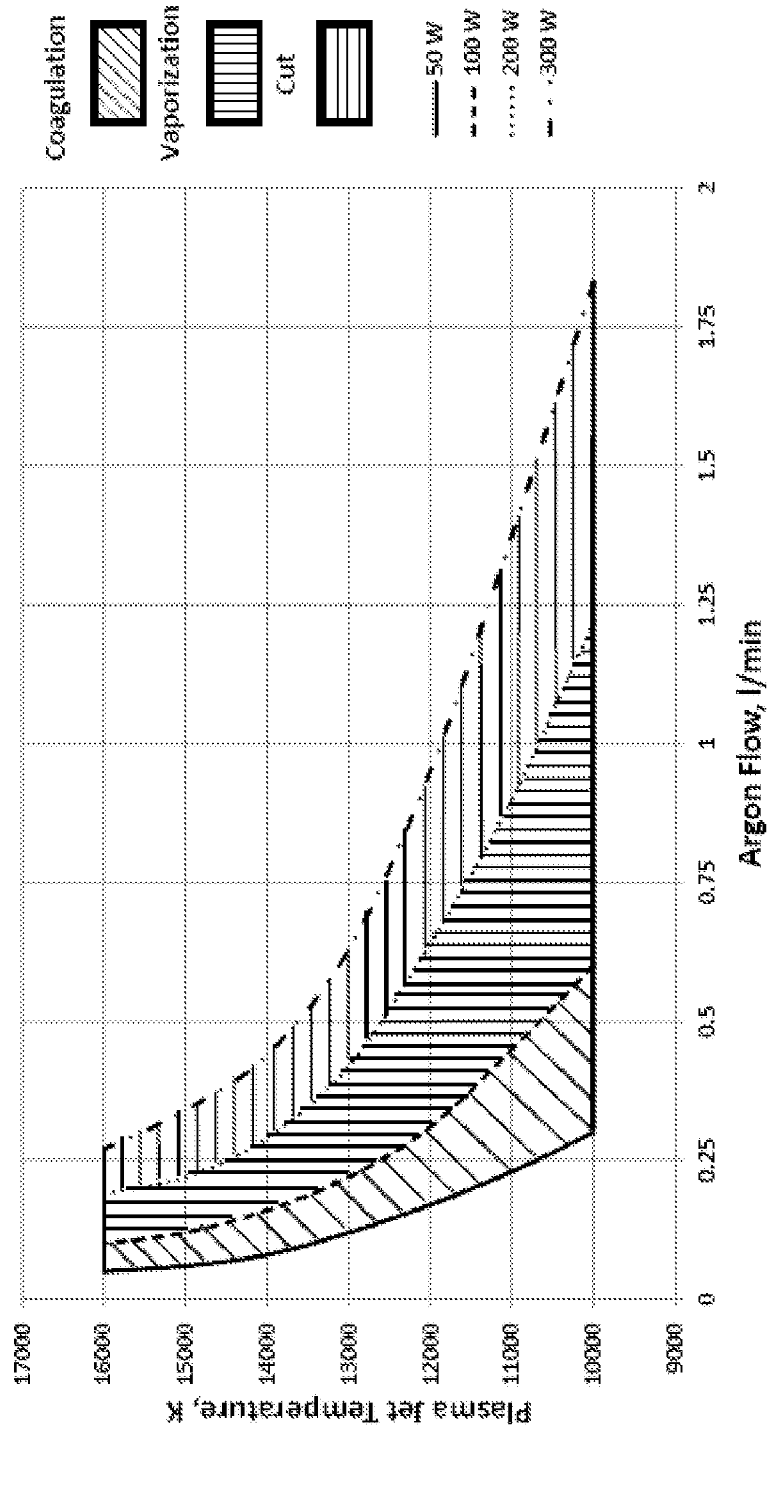
FIG. 5 shows the relationship between the temperature of a plasma flow and the plasma-generating gas flow rate at different operating power levels.

FIG. 5 shows the relationship between the temperature of the discharged plasma flow and the plasma-generating gas flow rate. To achieve the desirable effect, such as coagulation, vaporization, or cutting at different power levels, a certain plasma-generating gas flow rate is required, as shown in FIG. 5. As described above, even with relatively low plasma-generating gas flow rates, it is possible to generate a plasma flow with a certain temperature, at a certain power level. At the same time, with relatively low plasma-generating gas flow rates, it is possible to keep the operating current below a predetermined threshold that is known not to be harmful to the treated patient.

It has been found that embodiments 1; 101; 201 of the plasma-generating devices shown in FIGS. 1*a*-3 enable the generation of a plasma flow with the desired properties. Thus, embodiments 1, 101, and 201 can be used to generate plasma flows suitable for cutting living biological tissue at safe operating currents and plasma-generating gas flow rates.

Preferred geometric relationships between parts of the plasma-generating device 1; 101; 201 are described below with reference to FIGS. 1*a*-1*b*. It is noted that the dimensions described below are only exemplary and can be varied depending on the application and the desired plasma properties. It is also noted that the examples given in connection with FIGS. 1*a*-*b* are applicable to embodiments shown in FIGS. 2-3.

The inner diameter $d_i$ of insulator sleeve 19 is only slightly greater than the outer diameter $d_c$ of cathode 5. In one embodiment, the area of the gap between insulator sleeve 19 and cathode 5 is equal to or greater than a cross-sectional area of the inlet of plasma channel 11 in a common cross-section.

Figure 1B:
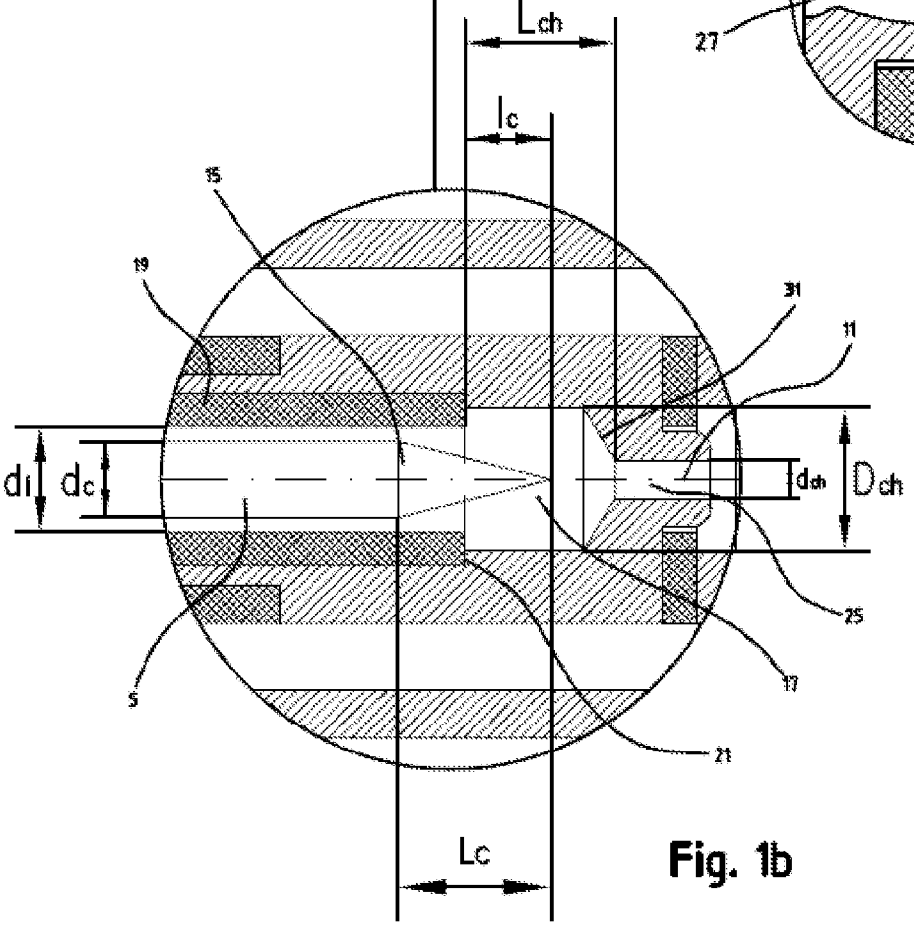
FIG. 1*b* is partial enlargement of the embodiment in FIG. 1*a;*

In the embodiment shown in FIG. 1*b*, the outer diameter $d_c$ of the cylindrical portion of cathode 5 is about 0.50 mm and the inner diameter $d_i$ of insulator sleeve 19 is about 0.80 mm.

In one embodiment, cathode 5 is arranged so that a partial length of cathode tip 15 projects beyond distal boundary surface 21 of insulator sleeve 19. In FIG. 1*b*, cathode tip 15 is positioned so that approximately half of cathode tip 15 length, $L_c$, projects beyond boundary surface 21. In the embodiment shown in FIG. 1*b*, the length by which cathode tip 15 projects beyond boundary surface 21, $l_c$, approximately equals to the diameter $d_c$ of cathode 5 at the base of tip 15.

The total length $L_c$ of cathode tip 15 is greater than 1.5 times the diameter $d_c$ of cathode 5 at the base of cathode tip 15. Preferably, the total length $L_c$ of the cathode tip 15 is about 1.5-3 times the diameter $d_c$ of cathode 5 at the base of cathode tip 15. In the embodiment shown in FIG. 1*b*, the length $L_c$ of cathode tip 15 is approximately 2 times the diameter $d_c$ of cathode 5 at the base of cathode tip 15.

In one embodiment, the diameter $d_c$ of cathode 5 at the base of cathode tip 15 is about 0.3-0.6 mm. In the embodiment shown in FIG. 1*b*, this diameter is about 0.50 mm. Preferably, cathode 5 has a uniform diameter $d_c$ between the base of cathode tip 15 and its proximal end. However, it should be appreciated that it is possible for cathode 5 to have a non-uniform diameter between the base of cathode tip 15 and the proximal end.

In one embodiment, plasma chamber 17 has a diameter $D_{ch}$ that is approximately 2-2.5 times the diameter $d_c$ of cathode 5 at the base of cathode tip 15. In the embodiment shown in FIG. 1*b*, plasma chamber 17 has the diameter $D_{ch}$ that is 2 times the diameter $d_c$ of the cathode 5 at the base of cathode tip 15.

The length $L_{ch}$ of plasma chamber 17 is approximately 2-2.5 times the diameter $d_c$ of cathode 5 at the base of cathode tip 15. In the embodiment shown in FIG. 1*b*, the length $L_{ch}$ of plasma chamber 17 is approximately equal to the diameter of the plasma chamber 17, $D_{ch}$.

In one embodiment, cathode tip 15 extends over at least a half of plasma chamber 17 length, $L_{ch}$. In an alternative embodiment, cathode tip 15 extends over ½ to ⅔ plasma chamber 17 length, $L_{ch}$. In the embodiment shown in FIG. 1*b*, cathode tip 15 extends at least half plasma chamber 17 length, $L_{ch}$.

In the embodiment shown in FIG. 1*b*, cathode 5 extends into plasma chamber 17 with its distal end positioned some distance away from plasma channel 11 inlet. This distance approximately equals the diameter $d_c$ of cathode 5 at the base of tip 15.

In the embodiment shown in FIG. 1*b*, plasma chamber 17 is in fluid communication with high pressure chamber 25 of plasma channel 11. High pressure chamber 25 has a diameter $d_{ch}$ in the range of 0.2-0.5 mm. In the embodiment shown in FIG. 1*b*, the diameter $d_{ch}$ of high pressure chamber 25 is about 0.40 mm. However, it should be appreciated that high pressure chamber 25 does not have to have a uniform diameter.

In some embodiments, as shown in FIG. 1*b*, plasma chamber 17 comprises a cylindrical portion and tapering transitional portion 31. In those embodiments, transitional portion 31 essentially bridges the cylindrical portion of plasma chamber 17 and high pressure chamber 25. Transitional portion 31 of plasma chamber 17 tapers downstream, from the diameter $D_{ch}$ of the cylindrical portion of plasma chamber 17 to the diameter $d_{ch}$ of high pressure portion 25. Transitional portion 31 can be formed in a number of alternative ways. In the embodiment shown in FIG. 1*b*, transitional portion 31 is formed as a beveled edge. Other transitions, such as concave or convex transitions, are possible. It should be noted, however, that the cylindrical portion of plasma chamber 17 and high pressure chamber 25 can be arranged in direct contact with each other without transitional portion 31. Transitional portion 31 facilitates favorable heat extraction for cooling of structures adjacent to plasma chamber 17 and plasma channel 11.

Plasma-generating device 1 can be a part of a disposable instrument. For example, an instrument may comprise plasma-generating device 1, outer shell, tubes, coupling terminals, etc. and can be sold as a disposable instrument. Alternatively, only plasma-generating device 1 can be disposable and be connected to multiple-use devices.

Other embodiments and variants are also contemplated. For example, the number and shape of the intermediate electrodes 9, 9', 9" can be varied according to the type of plasma-generating gas used and the desired properties of the generated plasma flow.

In use, the plasma-generating gas, such as argon, is supplied to the gap formed by the outer surface of cathode 5 and the inner surface of insulator sleeve 19, through the gas supply part, as described above. The supplied plasma-generating gas is passed on through plasma chamber 17 and through plasma channel 11. The plasma-generating gas is discharged through the outlet of plasma channel 11 in anode 7. Having established the gas supply, a voltage system is switched on, which initiates an electric arc discharge process in plasma channel 11 and ignites an electric arc between cathode 5 and anode 7. Before establishing the electric arc, it is preferable to supply coolant to various elements of plasma-generating device 1 through auxiliary channels 23, as described above. Having established the electric arc, plasma is generated in plasma chamber 17. The plasma is passed on through plasma channel 11 toward the outlet thereof in anode 7. The electric arc established in plasma channel 11 heats the plasma.

A suitable operating current for the plasma-generating devices 1, 101, 201 in FIGS. 1-3 is 4-10 Amperes, preferably 4-8 Amperes. The operating voltage of the plasma-generating device 1, 101, 201 depends, among others, on the number of intermediate electrodes and the length of the intermediate electrodes. A relatively small diameter of the plasma channel enables relatively low energy consumption and relatively low operating current when using the plasma-generating device 1, 101, 201.

The center of the electric arc established between cathode 5 and anode 7, along the axis of plasma channel 11, has a prevalent temperature T. Temperature T is proportional to the quotient of discharge current I and the diameter $d_{ch}$ of plasma channel 11 according to the following equation: $T=K*I/d_{ch}$. To provide a high temperature of the plasma flow, for example 11,000 to 20,000° C. at the outlet of plasma channel 11 in anode 7, at a relatively low current level I, the cross-section of plasma channel 11, and thus the cross-section of the electric arc should be small. With a small cross-section of the electric arc, the electric field strength in plasma channel 11 tends to be high.

The different embodiments of a plasma-generating device according to FIGS. 1*a*-3 can be used, not only for cutting living biological tissue, but also for coagulation and/or vaporization. An operator, with relatively simple hand motions, can switch the plasma-generating device to a selected mode of coagulation, vaporization, or cutting.

What is claimed:

1. A plasma-generating device comprising:

a. an anode at a distal end of the device, the anode having a hole therethrough;

b. a plurality of intermediate electrodes electrically insulated from each other and from the anode, each of the intermediate electrodes having a hole therethrough, wherein the holes in the intermediate electrodes and the hole in the anode, at least in part, form a hollow space having i. a first portion having a throat, the throat having a first cross-sectional area, ii. a second portion, which over a substantial length of this portion has a uniform second cross-sectional area larger than the first cross-sectional area, the second portion being formed by two or more of the intermediate electrodes, the second portion being upstream of the first portion, iii. a third portion, which over a substantial length of this portion has a uniform third cross-sectional area larger than the first cross-sectional area, the third portion, at least in part, being formed by the anode, the third portion being downstream of the first portion;

c. a cathode having a tapered portion; and d. an insulator sleeve extending along and surrounding a substantial portion of the cathode, wherein an inside surface of the insulator sleeve and an outside surface of the cathode form a gap, the gap being in communication with the hollow space.

2. The plasma-generating device of claim 1 further comprising an outer sleeve.

3. The plasma-generating device of claim 2, wherein the outer sleeve and the anode are parts of an integral structure.

4. The plasma-generating device of claim 1 further comprising an insulator positioned between a pair of adjacent intermediate electrodes of the plurality of intermediate electrodes, and an insulator positioned between a distal-most intermediate electrode and the anode.

5. The plasma-generating device of claim 1, wherein a distal portion of the cathode is tapered, and the tapered portion partially projects beyond a distal end of the insulator sleeve.

6. The plasma-generating device of claim 1, wherein the first portion of the hollow space is formed by one of the intermediate electrodes.

7. The plasma-generating device of claim 1, wherein the first portion of the hollow space is a supersonic nozzle.

8. The plasma-generating device of claim 7, wherein the hollow space has a fourth portion, which over a substantial length of this portion has a uniform fourth cross-sectional area, the fourth cross-sectional area being larger than the second cross-sectional area and the third cross-sectional area, the fourth portion being upstream of the second portion of the hollow space.

9. The plasma-generating device of claim 8, wherein the fourth portion is formed by a proximal-most of the intermediate electrodes.

10. The plasma-generating device of claim 9, wherein a distal end of the cathode is positioned inside the fourth portion of the hollow space.

11. The plasma-generating device of claim 8, wherein the fourth and second portions of the hollow space are connected through a transitional fifth portion of the hollow space tapering toward the anode.

12. The plasma-generating device of claim 8, wherein the fourth portion of the hollow space extends from a distal end of the insulator sleeve to a proximal end of the second portion of the hollow space.

13. A plasma surgical instrument comprising the plasma-generating device of claim 1.

14. The plasma surgical instrument of claim 13 adapted for laparoscopic surgery.

15. The plasma surgical instrument of claim 14 having an outer cross-sectional width of under 10 mm.

16. The plasma surgical instrument of claim 15 having an outer cross-sectional width of under 5 mm.

17. A method of using the plasma surgical instrument of claim 13 comprising a step of discharging plasma from a distal end of the plasma surgical instrument on a biological tissue.

18. The method of claim 17 further comprising one or more steps of: cutting, vaporizing, and coagulating the biological tissue.

19. The method of claim 17, wherein the discharged plasma is substantially free of impurities.

20. The method of claim 17, wherein the biological tissue is one of liver, spleen, heart, brain, kidney, or bone.

21. A method of generating plasma comprising a step of supplying to the plasma-generating device of claim 1 a plasma-generating gas at a rate of 0.05 to 1.00 1/min and establishing an electric arc of 4 to 10 Amperes between the cathode and the anode.

22. The method of claim 21, wherein the plasma-generating gas is an inert gas.

* * * * *